United States Patent [19]

Klafta

[11] Patent Number: 5,065,755
[45] Date of Patent: Nov. 19, 1991

[54] PROTECTIVE SHEATH FOR CUFF OR SINGLE OR DOUBLE LUMEN ENDOTRACHEAL TUBE

[76] Inventor: Jerome M. Klafta, 211 E. Ohio, Apt. 1412, Chicago, Ill. 60611

[21] Appl. No.: 442,852

[22] Filed: Nov. 29, 1989

[51] Int. Cl.⁵ .............................................. A61M 16/00
[52] U.S. Cl. ............................ 128/200.26; 128/207.15
[58] Field of Search ................... 128/200.26, 207.14, 128/207.15

[56] References Cited

U.S. PATENT DOCUMENTS

| | | | |
|---|---|---|---|
| 3,616,799 | 11/1971 | Sparks | 128/207.15 |
| 4,693,243 | 9/1987 | Buras | 128/207.15 |
| 4,782,829 | 11/1988 | Weiss | 128/207.15 |

Primary Examiner—Edgar S. Burr
Assistant Examiner—Aaron J. Lewis
Attorney, Agent, or Firm—Laff, Whitesel, Conte & Saret

[57] ABSTRACT

A protective sheath for an endotracheal tube, the sheath being manually positioned onto the endotrocheal tube and covering and protecting a cuff of the tube during insertion of the tube into a patient. The sheath is removable from the tube after insertion of the endotracheal tube into the patient. The sheath comprises a generally cylindrical body and a retrieval member, with the retrieval member being attached to one end of the generally cylindrical body and providing a removal mechanism for the sheath from the endotracheal tube after intubation.

19 Claims, 4 Drawing Sheets

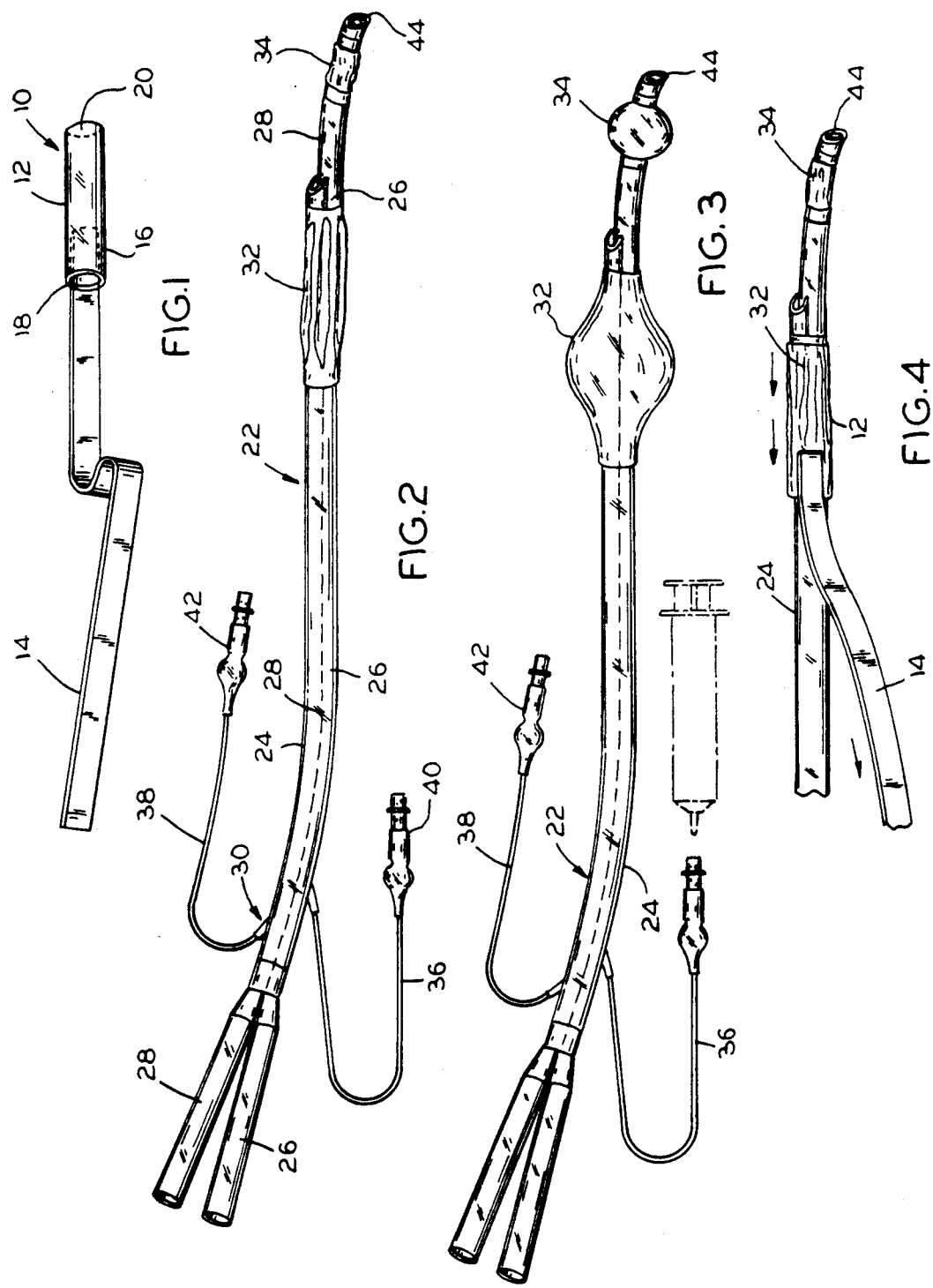

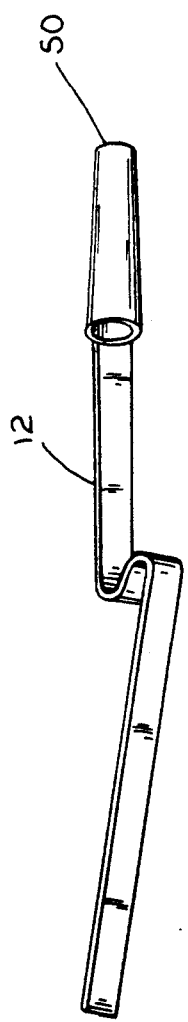
FIG.7
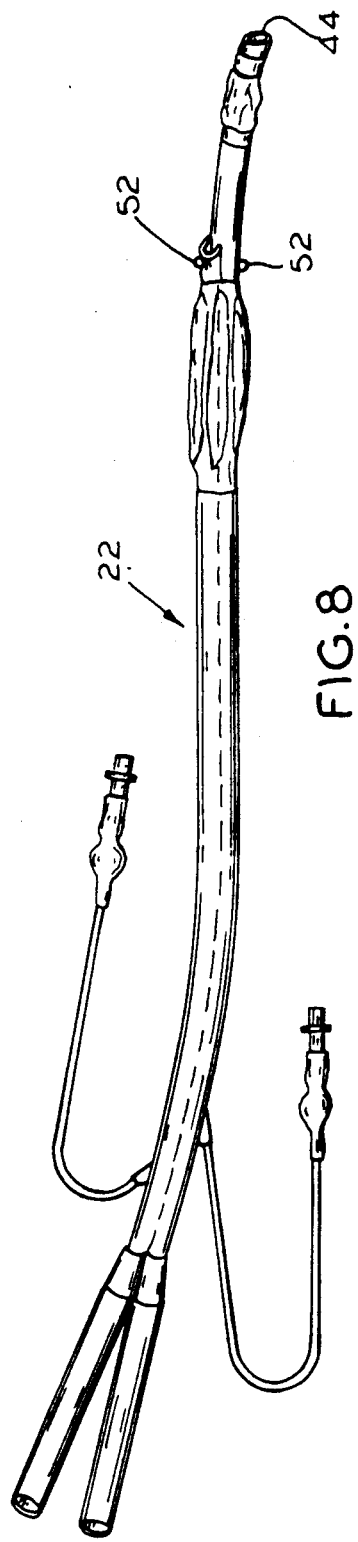
FIG.8
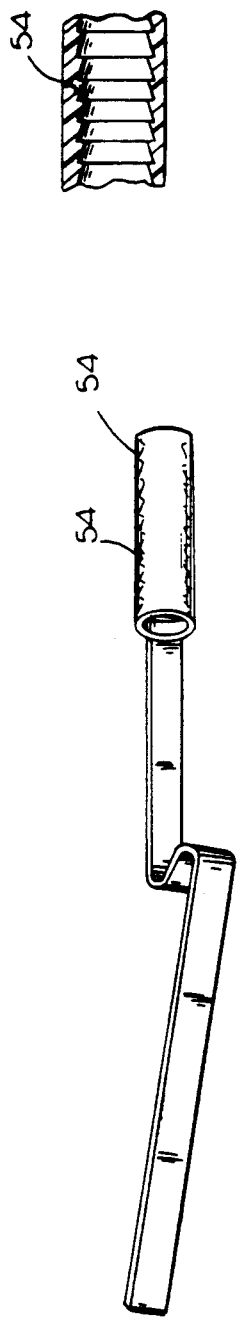
FIG.9A
FIG.9

PROTECTIVE SHEATH FOR CUFF OR SINGLE OR DOUBLE LUMEN ENDOTRACHEAL TUBE

FIELD OF THE INVENTION

This invention relates to a disposable protective apparatus for an endotracheal tube having a single or double lumen. More particularly, this invention relates to a disposable protective introducer or sheath for an endotracheal tube that prevents cuff tears and punctures during intubation.

BACKGROUND OF THE INVENTION

It is a common practice to provide human medical patients with artificial ventilation means during surgery or in emergency situations. For example, frequently accident victims require CPR or intubation by the paramedic in an emergency vehicle or by an anesthesiologist in an operating room. Intubation is accomplished by insertion of an endotracheal tube into the patient's airway passage. The endotracheal tube may be either a single lumen endotracheal tube or a double lumen endotracheal tube. The single lumen endotracheal tube is an elongated tube that extends into the trachea of a patient upon intubation and includes one inflatable cuff on its distal end. The double lumen endotracheal tube is commonly referred to as an endobronchial tube and not only has one lumen which extends into the trachea, but a further longer lumen which extends into the bronchus upon intubation. The double lumen endotracheal tube or endobronchial tube includes two inflatable cuffs on its distal ends, as will be further discussed. The present invention relates to both the single lumen endotracheal tube and the double lumen endotracheal tube.

The single lumen endotracheal tube is inserted into the patient by placing it first into the patient's oral cavity and then manually manipulating the tube through the vocal cords and into the tracheal cavity. As stated above, similar manipulation is used to insert the double lumen endotracheal (endobronchial) tube into the patient, wherein the first lumen extends into the trachea, and the second lumen into the bronchus. A laryngoscope is utilized during the insertion of each endotracheal tube to lift the patient's tongue and to provide direct visualization of the vocal cords.

The single lumen and the double lumen endotracheal tubes each include an inflatable, balloon-like upper tracheal cuff near its distal end. The double lumen endotracheal tube further includes a smaller lower bronchial cuff on the distal end of the longer bronchial lumen. The cuffs are thin walled, high volume and low pressure, and are designed so as not to compromise the blood flow in the tracheal or bronchial wall when inflated. The cuffs are inflated by detachable syringes that are connected to channels at the proximal end of the endotracheal tube and function to form seals between the tube and the inner walls of the trachea, and further in the bronchus in the double lumen endotracheal tube. The seals formed by the inflated cuffs preclude the air that has been forced into the patient's lungs from escaping through the trachea or bronchus. Additionally, the seals formed by the inflated cuffs provide a barrier to blood and secretions. The cuffs are extremely thin to facilitate passage of the tube through the oral cavity and subsequent inflation and accordingly, are susceptible to tearing.

The insertion of existing prior art single and double lumen endotracheal tubes is often a problem due to difficult airways in the patient caused by unusual anatomy or other abnormalities of the teeth or oral cavity. Insertion of the tubes into the patient's oral cavity is further complicated by the bulky and cumbersome shape of the tube which serves to further exacerbate existing difficulties. Because of the awkward design of the tube in conjunction with the fragility of the cuffs, the cuffs frequently tear on the patient's teeth or are punctured by the laryngoscope blade during the intubation process. The tracheal cuff is especially susceptible to tears due to its larger diameter and its increased exposure to the patient's oral cavity. Moreover, the laryngoscope is positioned and maintained in the oral cavity after the smaller bronchial cuff of the double lumen endotracheal tube has passed through the oral cavity and is being manipulated past the vocal cords and into the bronchus. Accordingly, it is the larger tracheal cuff of both the single and double lumen endotracheal tube which is primarily exposed to the laryngoscope and to the patient's teeth.

When a tear occurs in the cuff, the tube must be removed from the patient and discarded, and the intubation process must be re-initiated and repeated until proper insertion of the tube is achieved. Not only is it expensive to replace the tubes due to a cuff tear, but the time involved in removal of the tube for replacement thereof may be critical to the survival of the patient.

Conventional attempts to prevent the cuff from tearing, such as repositioning the jaw, lubricating the cuff, and padding the teeth have proven to be ineffective.

SUMMARY OF THE INVENTION

The present invention, by contrast with the above-mentioned endotracheal tubes, is concerned primarily with providing a disposable protective sheath that covers and protects the cuff, specifically the larger tracheal cuff, of a single and double lumen endotracheal tube during the intubation process. Subsequent to proper intubation, the sheath may be manually removed from the tube by simply pulling on a flexible ribbon-like member or retrieval mechanism attached thereto. The sheath is thin walled so that it does not materially increase the diameter of the endotracheal tubes and does not affect the intubation process. The diameter of the sheath is such that it will not slide up the exterior of the tube during intubation. In the rare case of the sheath riding up on the tube when passing between the vocal cords, the cuff is already past the danger areas, i.e. the oral cavity and laryngoscope blade, and is therefore positioned in the tracheal cavity without tearing or puncturing. Accordingly, the use of this protective sheath precludes cuff tears and eliminates removal of the tube for replacement during the intubation process. Thus, critical time is not lost during an emergency situation.

Accordingly, an object of the present invention is to provide a protective introducer or sheath for the tracheal cuff of both a single and double lumen endotracheal tube that prevents cuff tears during intubation.

Another object of the present invention is to provide a protective sheath that greatly increases the percentage of successful first attempts at intubation of single and double lumen endotracheal tubes by reducing cuff tears.

Another object of the present invention is to provide a protective sheath for the cuff of both a single and double lumen endotracheal tube that is disposable.

Another object of the present invention is to provide a protective sheath for the cuff of a single and double lumen endotracheal tube having a retrieval mechanism by which the sheath can be recovered after successful intubation and which permits normal cuff inflation.

A further object of the present invention is to provide a protective sheath for the cuff of a single and double lumen endotracheal tube that is adapted to fit any existing single and double lumen endotracheal tube and which may be quickly and easily attached to any endotracheal tube.

A further object of the present invention is to provide a protective sheath for the cuff of a single or double lumen endotracheal tube that is easy to manufacture and cost effective to use.

In the preferred embodiment, the invention comprises a thin, cylindrical sheath that covers and protects the cuff. The diameter of the sheath is such that the sheath is adapted to fit snugly over the cuff yet still be slideably moveable over the tube. The sheath includes a retrieval mechanism which ensures that the sheath can be recovered once the tube is properly positioned in the patient. The retrieval mechanism is essentially a ribbon-like element or tether that allows traction on the sheath from a distance. The tether is attached to the end of the sheath closest to the proximal portion of the single and double lumen endotracheal tube. The tether is not attached at its other end, which is adapted to be gripped by the medical personnel inserting the single or double lumen endotracheal tube.

In the preferred embodiment, the sheath is threaded over the distal end of the single or double lumen endotracheal tube and positioned over the cuff so that the retrieval mechanism lies along the convexity of the tube. Because the force hitting the sheath is usually radial, the sheath will not slide towards the proximal end of the endotracheal tube. After intubation, the sheath is easily pulled back into the oral cavity via the tether, cut and removed.

In another embodiment, the end of the sheath closest to the distal end of the tube is slightly tapered so that it will not catch on any objects in the oral cavity or on the vocal cords.

In yet another embodiment, the single and double lumen endotracheal tube includes at least one boss beneath the cuff on its distal end, and on opposite sides of the tube, to prevent the sheath from being left behind in the patient during removal of the tube in the unlikely event of failure of the retrieval mechanism.

In yet another embodiment, the sheath includes a retention loop which is attached at both ends to a flexible retrieval mechanism of the sheath so that the retrieval mechanism will remain close to the endotracheal tube.

In yet a further embodiment, the sheath includes notches that are angled towards the distal end of the tube so that the sheath will not be left behind during removal of the tube from the patient.

All of the aforementioned embodiments contemplate a removably attached sheath that is constructed preferably from a plastic material, or any other suitable material, including but not limited to stiff cellophane material. The sheath may include strengthening elements, for example, nylon threads, which may be included for additional support. The retrieval mechanism that is attached to the sheath may be made of similar or other suitable materials.

Thus, the present invention provides a removably slidable sheath that covers and protects the tracheal cuff from the teeth, the laryngoscope blade and other obstacles in the oral cavity. The sheath includes a retrieval mechanism for removal of the sheath when the tracheal cuff is at least part way through the vocal cords, such positioning of the cuff as may be ascertained visually. The inventive device is inexpensive to manufacture, yet is sturdy and durable and solves a problem that has not been addressed in the prior art. The present invention is particularly useful since the large caliber of the tube and the position of the tracheal cuff exacerbate existing difficulties.

The above, as well as other objects and advantages of the invention, will become apparent from the following detailed description of the preferred embodiments, reference being made to the accompanying drawings.

BRIEF DESCRIPTION OF THE DRAWINGS

FIG. 1 is a perspective view of the inventive sheath, as it would appear prior to insertion on both a single lumen and double lumen endotracheal tube.

FIG. 2 is a perspective view of a double lumen endotracheal (endobronchial) tube illustrating the uninflated cuffs and prior to the insertion of the inventive device of FIG. 1.

FIG. 3 is a perspective view of the double lumen endotracheal tube of FIG. 2 with inflated cuffs.

FIG. 4 is a fragmented perspective view of the inventive device of FIG. 1 positioned on the cuff of the tube of FIG. 2.

FIG. 7 is a perspective view of another embodiment of the sheath of FIG. 1, illustrating a slightly tapered distal end.

FIG. 8 is a perspective view of another embodiment of the double lumen endotracheal tube of FIG. 2, illustrating at least two bosses distal to the cuff and on opposite sides of the tube.

FIG. 9 is a perspective view of another embodiment of the sheath of FIG. 1, illustrating angled notches in the inventive sheath.

FIG. 9A is a fragmentary perspective view of the sheath of the embodiment in FIG. 9.

DETAILED DESCRIPTION OF THE INVENTION

Figure 5:
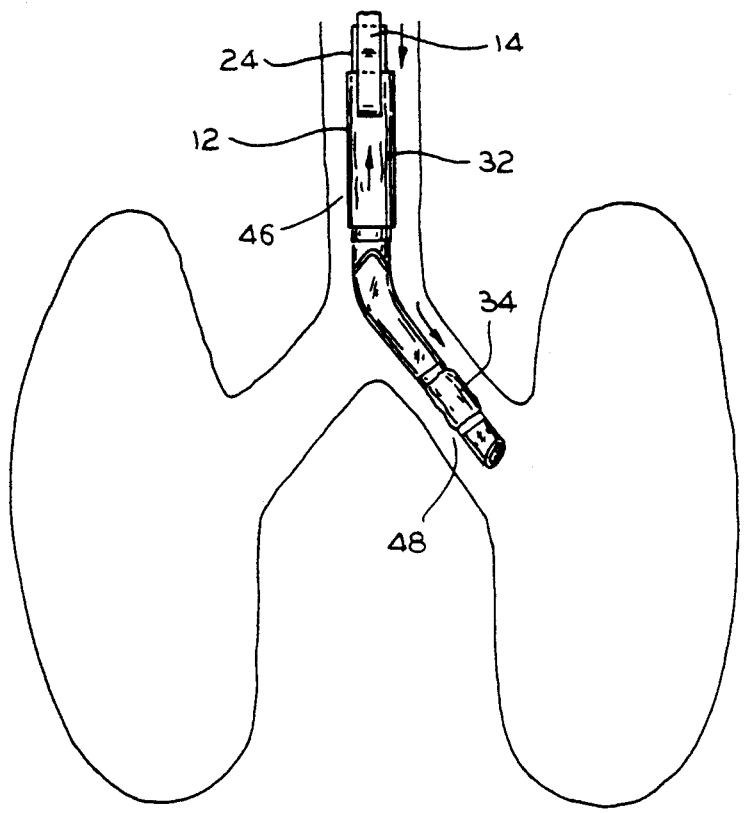
FIG. 5 is a perspective view of the inventive device as it would appear on a double lumen endotracheal tube during intubation.

Referring first to FIG. 1, the invention provides a disposable protective introducer device generally denoted by the numeral 10 having a generally hollow cylindrical body or sheath 12 and a flexible retrieval mechanism 14 attached to sheath 12 at point 16. Sheath 12 has two openings, 18 and 20, that are adapted to be threaded over a single lumen or a double lumen endotracheal tube. Opening 20 faces the distal end of the endotracheal tube after insertion of the sheath 12 onto the tube. Accordingly, opening 18 is closest to the proximal end of the tube. In the preferred embodiment, openings 18 and 20 are equal in diameter. In an alternate embodiment, opening 20 is slightly tapered inward to preclude the possibility of snagging a vocal cord during intubation. The overall diameter of sheath 12 is approximately equal to or slightly larger than the diameter of either the single lumen or double lumen endotracheal tube.

Figure 10:
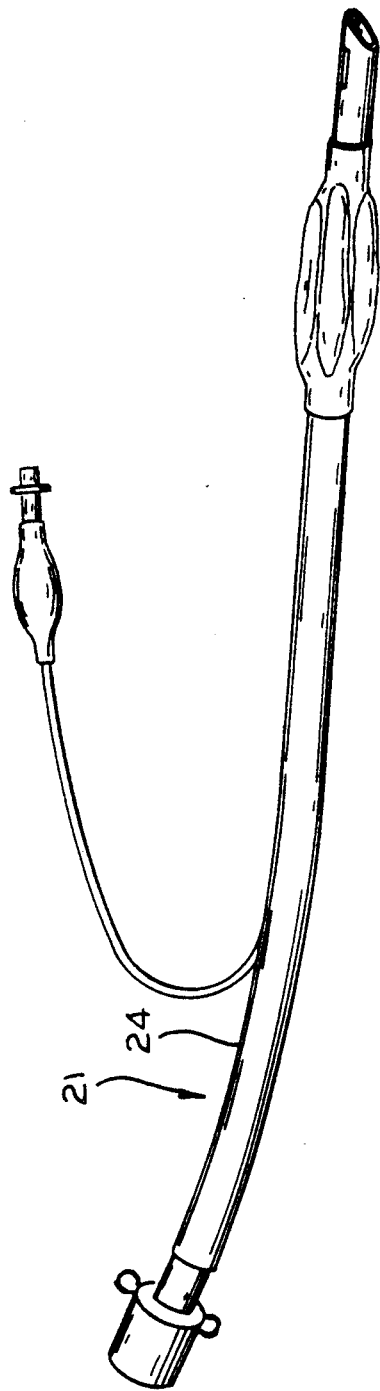
FIG. 10 is a perspective view of a single lumen endotracheal 5 tube illustrating the uninflated cuff and prior to the insertion of the inventive device of FIG. 1.

As shown in FIGS. 2 and 10, the inventive sheath 12 is threaded onto either a single lumen (FIG. 10) or double lumen endotracheal tube (FIG. 2), generally denoted by the numerals 21 and 22, respectively. The double lumen endotracheal tube 22 comprises, in part, a generally elongated cylindrical tube 24 which is divided into two separate ducts, specifically, a tracheal duct 26 and a bronchial duct 28. The single lumen endotracheal tube 21 is similar to the double lumen endotracheal tube 22 except that it does not have a bronchial duct, as illustrated in FIG. 10. Both tubes have a tracheal duct 26, which is that part of the tube 22 which is positioned in the trachea, and bronchial duct 28 is that part of the tube which rests in the bronchus following intubation. In the double lumen endotracheal tube 22, the tracheal and bronchial ducts 26, 28 are initially separated at the proximal end 30 of tube 24 but then extend side by side towards the distal end 44, with the bronchial duct 28 extending a distance further than the tracheal duct 26.

An inflatable tracheal cuff 32 is located near the distal end 44 of tube 24. Similarly, an inflatable bronchial cuff 34 is located between the distal end 32 of tube 24 and tracheal cuff 32. Tracheal cuff 32 and bronchial cuff 34 may be independently inflated by individual channels 36 and 38, which extend along the length of tube 22 and are attached to their respective cuffs. A syringe 37 is used to introduce air into head 40, 42 of channels 36, 38, respectively, which causes tracheal cuff 32 and bronchial cuff 34 to inflate, as shown in FIG. 3. Because the single lumen endotracheal tube 21 does not have a bronchial duct, the tube 21 has only an inflatable tracheal cuff, which is inflated in the above-described manner.

FIG. 4 shows the inventive sheath 12 as it would appear threaded over the distal end 44 of either the single lumen or double lumen endotracheal tube 24 prior to the intubation process. Sheath 12 is initially threaded onto the tip of distal end 44 of tube 24 through its opening 18. The sheath 12 is positioned directly over tracheal cuff 32 while the cuff 32 is in its deflated state. The retrieval mechanism 14 extends freely towards the proximal end 30 of tube 24. A small amount of lubrication is generally used on tube 24 prior to threading sheath 12 thereon for ease of application.

Figure 6:
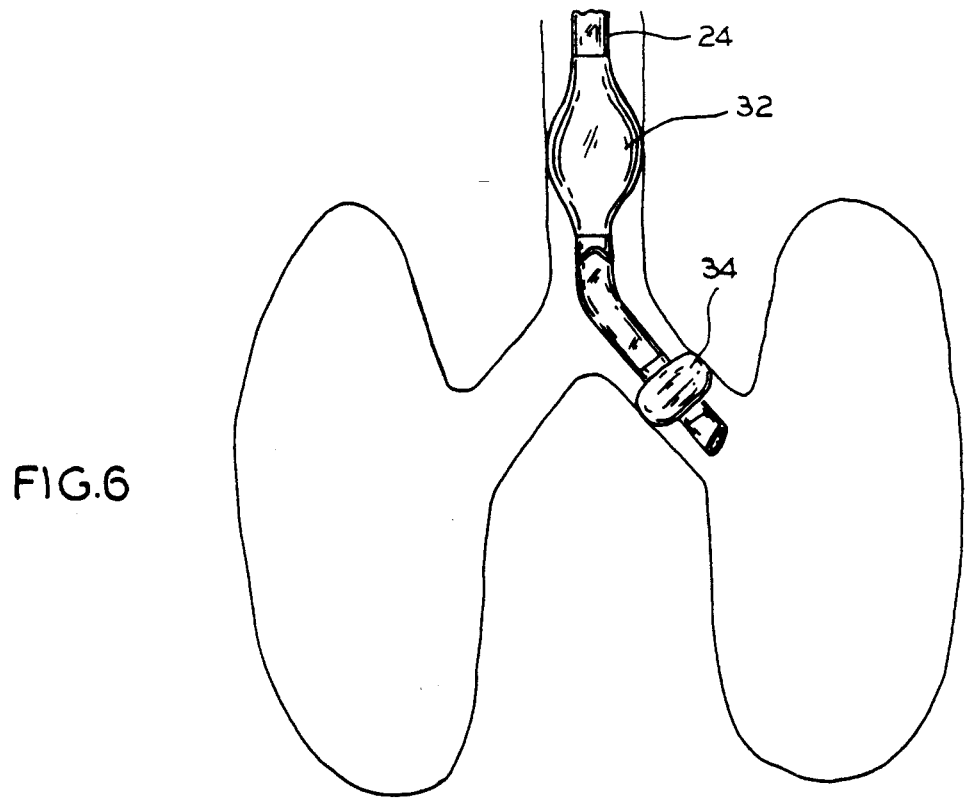
FIG. 6 is a perspective view of the double lumen endotracheal tube of FIG. 5 as it would appear after the completion of intubation and removal of the protective sheath.

FIGS. 5 and 6 show the double lumen endotracheal tube 22 in position after intubating the patient. Intubation using the single lumen endotracheal tube 21 is affected in the same manner. As FIG. 5 depicts, tube 24 is manually manipulated, in the direction indicated by the arrows, through the patients oral cavity and into the tracheal cavity 46 and then finally into the bronchial cavity 48. Sheath 12 is positioned over the deflated tracheal cuff 32 during the insertion and positioning of either the single lumen or double lumen endotracheal tube 24 into the patient's cavity, preventing the patient's teeth or any instruments from contacting and possibly ripping or puncturing tracheal cuff 32. FIG. 5 shows that the retrieval mechanism 14 extends upward and is parallel to the tube 24 during the insertion process. After the tube passes at least part way through the vocal cords, the distal end of retrieval mechanism 14 extends out of the oral cavity of the patient, whereby the sheath 12 can be easily pulled by the retrieval mechanism 14 away from the tracheal cuff 32 and towards the proximal end 30 of tube 24. When the sheath 12 is pulled from the tracheal cuff 32 and appears in the oral cavity, the sheath 12 is cut and removed.

FIG. 6 shows the double lumen endotracheal tube 24 as it appears correctly positioned in the patient's cavity and subsequent to the removal of sheath 12. It is at this stage that the physician or attendant manually inflates the tracheal cuff 32 and bronchial cuff 34 to prevent air from passing from the lungs out of the trachea or bronchus.

FIGS. 7-9 illustrate embodiments which provide sheath 12 of either single lumen or double lumen endotracheal tubes 21, 22 with different mechanisms which prohibit sheath 12 from sliding off of tubes 21, 22.

FIG. 7 shows an embodiment of sheath 12 having a slightly tapered opening 50 which is closest to the distal end of single lumen or double lumen endotracheal tubes 21, 22 after insertion of the sheath 12 onto the tube 21, 22. The tapered end 50 frictionally engages the outer circumference of the distal end of tube 22, and provides a smooth transition of the sheath 12 past the vocal cords, so as to lessen the possibility of damaging the vocal cords. The tapered end 50 is designed such that as a force is applied to retrieval mechanism 14, sheath 12 slides over tube 22 to expose tracheal cuff 32. In the unlikely event that retrieval mechanism 14 is damaged, upon removal of tube 22 from the trachea, tapered end 50 of sheath 12 provides sufficient gripping force to enable the sheath to remain attached to the tube 22 as the tube is withdrawn from the trachea. Therefore, the tapered end 50 prevents the sheath 12 from accidentally being left in the patient upon removal of tube 22.

FIG. 8 shows a further embodiment of a double lumen endotracheal tube 22 which includes at least two small bosses 52 below and on the side of the tracheal cuff 32 towards the distal end 44 of the tube 22 and on opposite sides of the tube 22. This embodiment may also be used on a single lumen endotracheal tube. The endotracheal tube 22 is squeezed in the area in which the bosses 52 are located so that sheath 12 may be inserted onto the tube 22. Upon removal of the endotracheal tube 22 from the patient, should some damage occur to retrieval mechanism 14, bosses 52 would prevent sheath 12 from slipping off the end of tube 22. Therefore, the sheath 12 would be removed from the patient along with tube 22.

FIG. 9 shows another embodiment of sheath 12 having a plurality of notches 54 which are inwardly disposed in sheath 12 and angled towards the distal end 44 of tubes 21, 22 after insertion of sheath 12 onto tubes 21, 22. The notches 54 may be more clearly visualized in FIG. 9A. Again, were damage to occur to retrieval mechanism 14, the notches 54 would enable the sheath 12 to frictionally grip the tube 22 as the tube was withdrawn from the trachea, thus preventing the sheath 12 from slipping off the end of tube 22 and accidentally being left in the patient.

Figure 11:
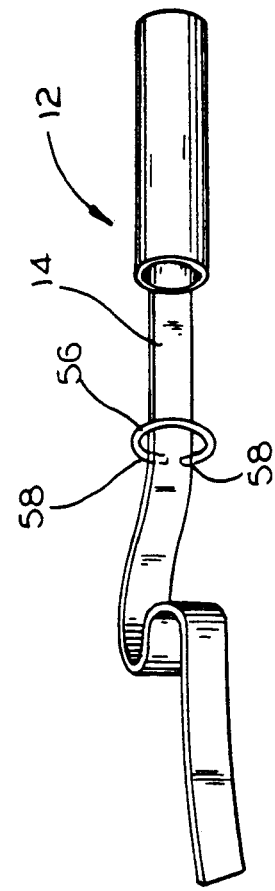
FIG. 11 is a perspective view of another embodiment of the sheath of FIG. 1, illustrating a retention loop forming part of the sheath.

FIG. 11 illustrates another embodiment of sheath 12 having a retention loop 56 which is attached at both ends to flexible retrieval mechanism 14 at section 58. Preferably, retention loop 56 is attached to retrieval mechanism 14 in the middle to lower third of the retrieval mechanism 14 nearest to sheath 12. The retention loop 56 is threaded over the distal end of the single or double lumen endotracheal tube at the same time the sheath 12 is inserted onto the tube. The retention loop 56 accordingly serves to retain retrieval mechanism 14 along the side of tube 24 of both the single and double lumen endotracheal tube 21, 22.

The protective introducer device 10 has not been described in terms of approximate measurements, as it should be understood that the size of the device 10 may vary according to the dimensions of the single lumen or double lumen endotracheal tubes 21, 22.

Therefore, it should be recognized that, while the invention has been described in relation to a preferred embodiment thereof, those skilled in the art may develop a wide variation of structural details without departing from the principles of the invention. Therefore, the appended claims are to be construed to cover all equivalents falling within the true scope and spirit of the invention.

What is claimed is:

1. In combination, a non-resilient protective sheath for an endotracheal tube, said sheath having a continuously cylindrical body and being manually positioned onto said endotracheal tube and covering a cuff of said endotracheal tube during insertion of said endotracheal tube into a patient; said sheath being removable from said endotracheal tube after insertion of said endotracheal tube into said patient; a retrieval member extending along the length of said endotracheal tube and attached to said sheath, whereby said sheath is removable from said cuff by means of said retrieval member after proper insertion of said endotracheal tube into said patient.

2. The combination of claim 1 wherein said endotracheal tube comprises a single lumen.

3. The combination of claim 1 wherein said endotracheal tube comprises a double lumen.

4. The combination of claim 1 wherein said endotracheal tube is an endobronchial tube.

5. The combination of claim 1 wherein said sheath is threaded over a distal end of said endotracheal tube and positioned over said cuff.

6. The combination of claim 1 wherein said retrieval member is approximately the length of the endotracheal tube.

7. The combination of claim 1 wherein said cuff located on said endotracheal tube is covered by said sheath when said cuff is in a deflated state.

8. The combination of claim 1 wherein said sheath is removed from said endotracheal tube by manually manipulating said retrieval member and causing said sheath to slide over said endotracheal tube towards its proximal end.

9. The protective sheath of claim 1 wherein said sheath is inwardly tapered at an end opposite to said end in which said retrieval member is attached.

10. The protective sheath of claim 1 wherein said endotracheal tube comprises boss means adjacent said cuff of said endotracheal tube.

11. The protective sheath of claim 1 wherein said sheath comprises notch means angularly disposed on an inner surface of said sheath in a direction towards a distal end of said endotracheal tube.

12. The protective sheath of claim 1 wherein said sheath includes a retention loop that is attached to said retrieval member of said sheath.

13. The combination of claim 1 wherein said retrieval member is a ribbon-like element attached to one end of said sheath.

14. In combination, a protective sheath for an endotracheal tube adapted to be inserted through the oral cavity and into the trachea of a patient receiving medical treatment, said endotracheal tube including duct means in said tube, cuff means extending around the circumference of a portion of said tube, inflation means connected to said cuff means, whereby said cuff means is adapted to be inflated after insertion of said tube in said trachea to prevent the passage of air alongside said tube, the improvement comprising:
   a non-resilient removable sheath having a continuously cylindrical body and being disposed over said cuff means, and retrieval means attached to said sheath and extending along said tube, said sheath being removable from over said cuff means after insertion of said tube in the trachea upon application of a force to said retrieval means;
   engaging means operative between said sheath and the outer surface of said endotracheal tube, whereby said sheath is adapted to be withdrawn with said endotracheal tube from said trachea upon a malfunction of said retrieval means, wherein said engaging means comprises a tapered portion of said sheath at a distal end of said sheath.

15. In combination, a protective sheath for an endotracheal tube adapted to be inserted through the oral cavity and into the trachea of a patient receiving medical treatment, said endotracheal tube including direct means in said tube, cuff means extending around the circumference of a portion of said tube, inflation means connected to said cuff means, whereby said cuff means is adapted to be inflated after insertion of said tube in said trachea to prevent the passage of air alongside said tube, the improvement comprising:
   a non-resilient removable sheath having a continuously cylindrical body and being disposed over said cuff means, and retrieval means attached to said sheath and extending along said tube, said sheath being removable from over said cuff means after insertion of said tube in the trachea upon application of a force to said retrieval means;
   engaging means operative between said sheath and the outer surface of said endotracheal tube, whereby said sheath is adapted to be withdrawn with said endotracheal tube from said trachea upon a malfunction of said retrieval means, wherein said engaging means comprises at least one boss element on said endotracheal tube, whereby the distal end of said sheath abuts said boss element.

16. The protective sheath of claim 1 wherein said sheath is disposable.

17. The combination of claim 1 wherein said sheath is disposable.

18. In combination, a non-resilient protective sheath for an endotracheal tube having a continuously cylindrical body, said sheath being manually positioned onto said endotracheal tube and covering a cuff of said endotracheal tube during insertion of said endotracheal tube into a patient; said sheath being removable from said endotracheal tube after insertion of said endotracheal tube into said patient; a retrieval member extending along the length of said endotracheal tube and attached to said sheath, whereby said sheath is removable from said cuff by means of said retrieval member after proper insertion of said endotracheal tube into said patient; said combination further comprising engaging means operative between said sheath and the outer surface of said endotracheal tube, whereby said sheath is adapted to be withdrawn with said endotracheal tube from said trachea upon a malfunction of said retrieval means, said engaging means comprises notch means angularly disposed on the inner surface of said sheath, said notch means frictionally gripping said endotracheal tube and extending in a direction toward the distal end of said endotracheal tube.

19. The combination of claim 18 wherein said endotracheal tube is an endobronchial tube.

* * * * *